United States Patent [19]

Suzuki et al.

[11] Patent Number: 4,462,930
[45] Date of Patent: Jul. 31, 1984

[54] HUMIDITY SENSOR

[75] Inventors: Toshihiko Suzuki, Aichi; Noboru Matsui, Seto, both of Japan

[73] Assignee: Kabushiki Kaisha Toyota Chuo Kenkyusho, Aichi, Japan

[21] Appl. No.: 446,034

[22] Filed: Dec. 1, 1982

[30] Foreign Application Priority Data

Dec. 7, 1981 [JP] Japan .................................. 56-196534

[51] Int. Cl.³ ............................................. H01B 1/06
[52] U.S. Cl. .................................... 252/519; 252/521; 338/35; 29/610 R; 73/73; 73/336.5
[58] Field of Search ........................ 252/519, 521, 518; 338/34, 35; 340/602; 73/73, 336.5; 264/61, 66, 104; 23/232 E; 29/592 R, 610 R; 75/211, 213, 214, 221, 200

[56] References Cited

U.S. PATENT DOCUMENTS

| | | | |
|---|---|---|---|
| 3,503,902 | 3/1970 | Shimoda | 252/519 |
| 3,926,858 | 12/1975 | Ichinose et al. | 252/521 |
| 4,015,230 | 3/1977 | Nitta et al. | 252/519 |
| 4,050,048 | 9/1977 | Frazee | 252/519 |
| 4,052,691 | 10/1977 | Nagano et al. | 252/521 |
| 4,086,556 | 4/1978 | Nitta et al. | 252/519 |
| 4,321,577 | 3/1982 | Carlson | 252/521 |
| 4,344,062 | 8/1982 | Sudoh et al. | 338/35 |
| 4,357,426 | 11/1982 | Murata et al. | 252/521 |
| 4,373,391 | 2/1983 | Johnson | 252/521 |

Primary Examiner—Josephine Barr
Attorney, Agent, or Firm—Oblon, Fisher, Spivak, McClelland & Maier

[57] ABSTRACT

A humidity sensor formed of a sintered compact consisting essentially of material substantially of a spinel structure represented by the formula: $M_{1-x}A_xFe_2O_{4-\alpha}$ where M stands for magnesium or zinc, A stands for an alkali metal, x is the numerical value in the range of 0.001 to 0.2, and $\alpha$ is the number of oxygen vacancies. The humidity sensor is highly sensitive over a wide relative humidity range, withstands a long use and presents almost no hysteresis in its humidity-resistance characteristics.

7 Claims, 2 Drawing Figures

HUMIDITY SENSOR

BACKGROUND OF THE INVENTION

1. Field of the Invention

This invention relates to a humidity sensor composed of a sintered compact of a metal oxide, and adapted to detect relative humidity as a change in electrical resistance.

2. Description of the Prior Art

A humidity sensor has a sensing portion which usually comprises a humidity-sensitive resistor composed of an organic polymer, such as a polyamide resin, polyvinyl chloride or polyethylene, or a metal oxide, such as $Fe_2O_3$ $Al_2O_3$, $Cr_2O_3$, or $V_2O_5$. A metal oxide is considered higher in chemical and physical stability, and more promising as a sensor material than an organic polymer.

Conventional metal oxides are, however, defective in a number of respects. For example, they are high in specific resistance, and have a low humidity dependence of resistance. A hysteresis exists in their humidity-resistance characteristics when they absorb and desorb moisture. Moreover, they fail to remain stable in a highly humid atmosphere for a long period of time. They are, therefore, not suitable as a material for humidity sensors.

SUMMARY OF THE INVENTION

The inventors of this invention have conducted repeated research and have reached the present invention which overcomes the aforesaid defects.

Accordingly, it is an object of the present invention to provide a humidity sensor having a high humidity sensitivity.

It is another object of the present invention to provide a humidity sensor having electrical resistance greatly changeable in response to the change in relative humidity.

It is still another object of the present invention to provide a humidity sensor having almost no hysteresis in its humidity-resistance characteristics.

It is a further object of the present invention to provide a humidity sensor which withstands a long period of use in a highly humid atmosphere.

It is a still further object of the present invention to provide a humidity sensor in which the humidity-resistance characteristics are hardly affected by the ambient temperature.

It is a further object of the present invention to provide a small humidity sensor having a quick response to the change of humidity.

The foregoing and other objects are attained by providing a humidity sensor comprising a sintered compact consisting essentially of material substantially of a spinel structure represented by the formula $$M_{1-x}A_xFe_2O_{4-\alpha}$$

where M stands for magnesium (Mg) or zinc (Zn), A stands for an alkali metal, x is a numerical value in the range of 0.001 to 0.2, and $\alpha$ is the number of oxygen vacancies.

The humidity sensor of this invention is very high in humidity sensitivity. Namely, its electrical resistance greatly changes in response to the change in relative humidity. The electrical resistance at relative humidity of 0% is in the range of as much as $10^2$ to $10^5$ times the electrical resistance at relative humidity of 100%.

DETAILED DESCRIPTION

Figure 1:
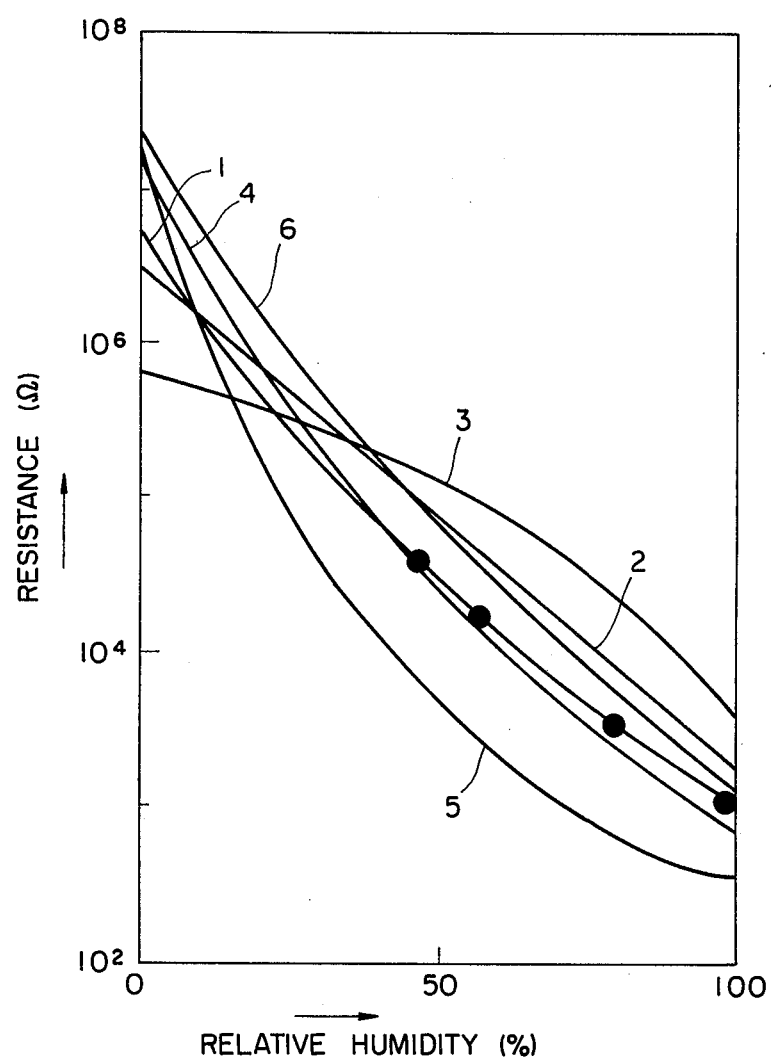
FIG. 1 is a graph showing the humidity-resistance characteristics of the humidity sensors embodying this invention.

The humidity sensor of this invention consists essentially of a metal oxide of the general formula $M_{1-x}A_x Fe_2O_{4-\alpha}$ obtained by substituting an alkali metal for 0.1 to 20 atom % of M in a spinel structure of the formula $MFe_2O_4$. The value of x should be in a range of 0.001 to 0.2 for obtaining the advantages as hereinabove set forth. The value of $\alpha$ depends on the quantity x of the alkali metal, and is equal to about a half of x (theoretically it is a half of x).

If x is 0.001 or less, the metal oxide has a lower humidity dependence of resistance. If x is 0.2 or more a great hysteresis undesirably appears as a result of the repeated moisture adsorption and desorption due to the presence of a structure other than a spinel structure, for example, a $\beta$-alumina structure. In either case, the metal oxide is unusable as a material for a humidity sensor.

If x is in the range between 0.01 and 0.05, the metal oxide shows a substantially linear humidity-resistance curve on a semilogarithmic scale, and provides a very convenient humidity sensor.

A process for manufacturing a humidity sensor according to this invention will now be described.

The starting material to be employed in the present invention is composed of (1) at least one material selected from the group consisting of magnesium oxide, magnesium carbonate, magnesium nitrate, zinc oxide, zinc carbonate and zinc nitrate, (2) at least one material selected from the group consisting of alkali metal oxides, alkali metal carbonates and alkali metal nitrates, and (3) at least one material selected from the group consisting of iron oxides, iron carbonates and iron nitrates. Examples of alkali metal oxides include lithium oxide; those of alkali metal carbonates include sodium carbonate, potassium carbonate and lithium carbonate; and those of alkali metal nitrates include sodium nitrate, potassium nitrate and lithium nitrate.

The materials (1) to (3) are weighed in predetermined proportions to satisfy the formula $M_{1-x}A_xFe_2O_{4-\alpha}$, and are fully pulverized and mixed uniformly. The resulting powder is formed into a compact under a high pressure, which is then calcined at a temperature (e.g. 800° C. to 1,000° C.) equal to or lower than that of the subsequent sintering step. The calcined compact is pulverized again, and the powder is pressed into a desired shape under a higher pressure. The resulting compact is sintered at a temperature ranging from 800° C. to 1,200° C. to allow the compact to remain porous to a desired degree, whereby the humidity sensor of this invention is obtained.

EXAMPLES

Six samples of the material for the humidity sensor according to this invention were prepared by selecting (1) one of magnesium oxide (MgO) and zinc oxide (ZnO), (2) one of potassium carbonate ($K_2CO_3$), sodium carbonate ($Na_2CO_3$) and lithium carbonate ($Li_2CO_3$), and (3) ferric oxide ($Fe_2O_3$), weighing those powders accurately as shown at 1 to 6 in Table 1, and mixing them together.

TABLE 1

| No. | Weight of Starting Material (g) | | | | | | Elemental Proportion (Calculated from starting material) |
|---|---|---|---|---|---|---|---|
| | MgO | ZnO | $K_2CO_3$ | $Na_2CO_3$ | $Li_2CO_3$ | $Fe_2O_3$ | |
| 1 | 24.73 | — | 0.87 | — | — | 100.0 | $Mg_{0.98}K_{0.02}Fe_2O_{\approx 3.99}$ |
| 2 | " | — | — | 0.66 | — | " | $Mg_{0.98}Na_{0.02}Fe_2O_{\approx 3.99}$ |
| 3 | " | — | — | — | 0.46 | " | $Mg_{0.98}Li_{0.02}Fe_2O_{\approx 3.99}$ |
| 4 | 23.97 | — | 2.16 | — | — | " | $Mg_{0.95}K_{0.05}Fe_2O_{\approx 3.975}$ |
| 5 | 22.71 | — | 4.33 | — | — | " | $Mg_{0.9}K_{0.1}Fe_2O_{\approx 3.95}$ |
| 6 | — | 49.93 | 0.87 | — | — | " | $Zn_{0.98}K_{0.02}Fe_2O_{\approx 3.99}$ |

About seven grams of each sample were formed under a pressure of 200 kg/cm² into a disk having a diameter of 20 mm and a thickness of 6 mm. The disks formed from Samples 1 to 5 were calcined at 1,000° C., while the disk formed from Sample 6 was calcined at 900° C., all for 1.5 hours. Each disk was, then, pulverized carefully in a mortar by a pestle, and the resulting powder was pressed again under a pressure of 1 ton/cm² into a disk having a diameter of 10 mm and a thickness of 1 mm. The disks formed from Samples 1 to 5 were sintered at 1,050° C., while the disk formed from Sample 6 was sintered at 950° C., all for 1.5 hours in the air, whereby six humidity sensors of different compositions were prepared in accordance with this invention.

The properties of the humidity sensors thus prepared were examined by connecting a lead wire thereto as will hereinafter be described. The both surfaces of each humidity sensor were polished with #2000 emery paper, and after they had been washed with acetone, the surfaces were coated with a ruthenium dioxide ($RuO_2$) paste. The humidity sensor coated with the paste was heated at 800° C. for three minutes in the open air to form a ruthenium dioxide electrode. A silver paste was applied to each electrode. Then, the sensor with the silver paste was heated at 750° C. for three minutes to form a silver film. A lead wire was soldered to the sensor. The properties of each humidity sensor were examined as will hereinafter be described.

An AC voltage of 1 V having a frequency of 1 KHz was applied to the humidity sensor through the lead wire, whereby its humidity-resistance characteristics were determined. The results obtained when an ambient temperature of 26° C. prevailed are shown in FIG. 1, in which the resistance is shown by a value obtained after elimination of any effect that the specific shape of the sensor might have on its resistance. The numbers alloted to the curves in FIG. 1 are those of the samples appearing in Table 1. As is obvious from FIG. 1, the humidity sensors of this invention show a great change in resistance over a relatively humidity range of 0 to 100%.

These tests were conducted during both the adsorption and desorption of moisture. In either event, all of the sensors showed the results which could be expressed by the curves appearing in FIG. 1, and none of the sensors indicated any hysteresis. The stability of the humidity sensor according to this invention was, then, examined over a long period of time. The humidity sensor prepared from Sample 1 was placed in a box having a constant relative humidity of 80%. After it had been left in the highly humid atmosphere for two months, it was removed from the box, and its humidity-resistance characteristics were examined. The results are shown by black dots in FIG. 1. The fact that all of the dots stay on curve 1 indicates that the sensor still possessed the properties which it had had when it was manufactured.

Another sensor was prepared from a composition of the formula $Zn_{0.98}Na_{0.02}Fe_2O_{\approx 3.99}$ in which the proportions of the elements were calculated from the starting materials, and its initial humidity-resistance characteristics were examined. A high temperature durability test (at 85° C.) and a high temperature-high humidity durability test (at 60° C. and a relative humidity of 95% or above) were conducted for 1,500 hours respectively, by employing a constant temperature bath and a constant temperature-humidity bath. After these tests had been conducted, the humidity-resistance characteristics of the sensor were examined, and compared with its initial characteristics. The sensor showed a change in characteristics of only 10% or less in terms of relative humidity, and was found superior in durability.

Figure 2:
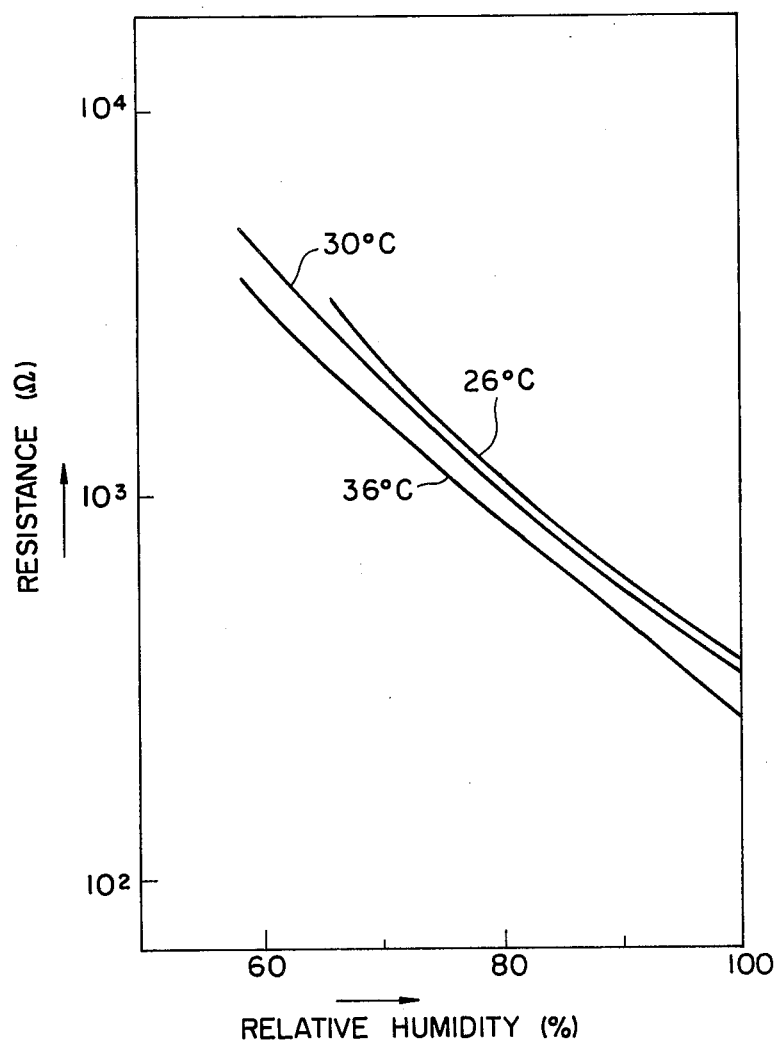
FIG. 2 is a graph showing by way of example changes in the humidity-resistance characteristics of the sensor with a change in temperature.

Further tests were conducted to examine the effect which the ambient temperature might have on the humidity sensor of this invention. Humidity sensors were prepared from Sample 4 of the material, and their humidity-resistance characteristics were examined at an ambient temperature of 26° C., 30° C. and 36° C., respectively. The results are shown in FIG. 2. As is obvious therefrom, the resistance of the humidity sensor according to this invention show a tendency to decrease with a rise in its ambient temperature, but only to such an extent that the decrease can be easily compensated by using a thermistor, or the like.

It is to be understood that within the scope of the appended claims, the invention may be practiced otherwise than as specifically described herein.

What is claimed is:

1. A humidity sensor having electrical resistance variable in response to the change of relative humidity, comprising a sintered compact consisting essentially of material of a spinel structure represented by the formula $$M_{1-x}A_xFe_2O_{4-\alpha}$$

where M stands for one of magnesium and zinc, A stands for an alkali metal selected from the group consisting of sodium, potassium and lithium, x is a numerical value in the range of 0.001 to 0.2 so that M is substituted with 0.1 to 20% of A, and $\alpha$ is the number of oxygen vacancies.

2. A humidity sensor according to claim 1, wherein x is in a range of 0.01 to 0.05.

3. A humidity sensor according to claim 1, wherein said electrical resistance at relative humidity of 0% is in the range of $10^2$ to $10^5$ times the value at relative humidity of 100%.

4. A method for producing a humidity sensor according to claim 1, comprising the steps of
    pulverizing into powder the mixture of (1) at least one material selected from the group consisting of magnesium oxide, magnesium carbonate, magnesium nitrate, zinc oxide, zinc carbonate and zinc nitrate, (2) at least one material selected from the group consisting of sodium oxide, potassium oxide, lithium oxide, sodium carbonate, potassium carbonate, lithium carbonate, sodium nitrate potassium nitrate and lithium nitrate, and (3) at least one material selected from the group consisting of iron oxides, iron carbonates and iron nitrates, said materials (1) to (3) being in predetermined proportions to satisfy said formula $M_{1-x}A_xFe_2O_{4-\alpha}$, where x is a numerical value in the range of 0.001 to 0.2 so that M is substituted with 0.1 to 20% of A, and $\alpha$ is the number of oxygen vacancies, pressing said powder into a desired-shaped compact under a high pressure, and sintering said compact at a temperature ranging from 800° C. to 1,200° C. to allow said compact to remain porous to a desired degree.

5. A method according to claim 4, wherein said mixture is composed of (1) one of magnesium oxide and zinc oxide, (2) one of sodium carbonate, potassium carbonate and lithium carbonate, and (3) ferric oxide.

6. A method according to claim 4, further comprising, before the step of said pulverizing, forming said mixture into a compact under a pressure lower than that in said pressing step, and calcining said compact at a temperature equal to or lower than that in said sintering step.

7. A method according to claim 6, wherein said temperature in said calcining is in the range of 900° C. to 1,000° C., and said temperature in said sintering is in the range of 950° C. to 1,050° C.

* * * * *